(12) United States Patent
Wessling et al.

(10) Patent No.: US 8,148,530 B2
(45) Date of Patent: Apr. 3, 2012

(54) PROCESS FOR THE PREPARATION OF 3.7-DIAZABICYCLO[3.3.1] NONANE COMPOUNDS

(75) Inventors: Michael Wessling, Kandern (DE); Barbara Duecker, Mainz (DE); Nicole Nitschke, Eschborn (DE)

(73) Assignee: Clariant Produkte (Deutschland) GmbH, Frankfurt (DD)

( * ) Notice: Subject to any disclaimer, the term of this patent is extended or adjusted under 35 U.S.C. 154(b) by 457 days.

(21) Appl. No.: 11/921,884

(22) PCT Filed: Jun. 10, 2006

(86) PCT No.: PCT/EP2006/005582
§ 371 (c)(1),
(2), (4) Date: Apr. 27, 2009

(87) PCT Pub. No.: WO2006/133869
PCT Pub. Date: Dec. 21, 2006

(65) Prior Publication Data
US 2009/0234124 A1     Sep. 17, 2009

(30) Foreign Application Priority Data
Jun. 15, 2005   (DE) .......................... 10 2005 027 619

(51) Int. Cl.
*C07D 471/04*     (2006.01)
(52) U.S. Cl. ...................................... 546/123
(58) Field of Classification Search ................... 546/123
See application file for complete search history.

(56) References Cited

U.S. PATENT DOCUMENTS

| 2003/0162681 A1 | 8/2003 | Hage et al. |
| 2011/0152528 A1 | 6/2011 | Sajitz et al. |
| 2011/0263857 A1 | 10/2011 | Sajitz et al. |

FOREIGN PATENT DOCUMENTS

| WO | WO 02/48301 A1 | 6/2002 |
| WO | WO 02/068574 A1 | 9/2002 |
| WO | WO 03/104234 A1 | 12/2003 |

OTHER PUBLICATIONS

Comba et al., European Journal of Inorganic Chemistry (2003), (9), 1711-1718.*
Comba et al., Helvetica Chimica Acta (2005), 88(3), 647-664.*
International Search Report for PCT/EP2006/005582, mail dated Oct. 12, 2006.
English Translation of International Preliminary Report on Patentability for PCT/EP2006/005582, issue dated Jan. 16, 2008.
Borzel, Heidi, et al, "Iron coordination chemistry with tetra-, penta- and hexadentate bispidine-type ligands", Inorganica Chimica Acta, 337(2002), pp. 407-419.
Siener, Tom et al: "Synthesis and Opioid Receptor Affinity of a Series of 2,4-Diary- Substituted 3,7-Diazabicyclononanones", Journal of Medicinal Chemistry, 43(2000), pp. 3746-3751, Sep. 13, 2000.

* cited by examiner

*Primary Examiner* — Janet Andres
*Assistant Examiner* — Niloofar Rahmani
(74) *Attorney, Agent, or Firm* — Tod A. Waldrop

(57) ABSTRACT

The present invention relates to a process for the preparation of 3,7-diazabicyclo[3.3.1]nonane compounds. According to the invention, in a first step, a dicarboxylic acid ester is reacted with a pyridine aldehyde and a primary amine. The piperidone which forms is reacted in a second stage with formaldehyde and a further primary amine. It is essential to the invention that, in the first reaction stage, a C2-C4-alcohol is used as solvent and, in the second reaction stage, a C3-C4-alcohol is used as solvent.

3 Claims, No Drawings

PROCESS FOR THE PREPARATION OF 3,7-DIAZABICYCLO[3.3.1] NONANE COMPOUNDS

The present invention is described in the German priority application No. 10 2005 027 619.9 filed Jun. 15, 2005, which is hereby incorporated by reference as is fully disclosed herein.

The invention relates to an improved process for preparing 3,7-diaza-bicyclo[3.3.1]nonane compounds which is performable on the industrial scale, affords reproducibly good yields and requires a lower solvent input.

3,7-Diazabicyclo[3.3.1]nonane compounds of the formula 1 are compounds of interest for various applications. Among other applications, they themselves or transition metal complexes which contain ligands of the formula (I) are very effective bleach catalysts

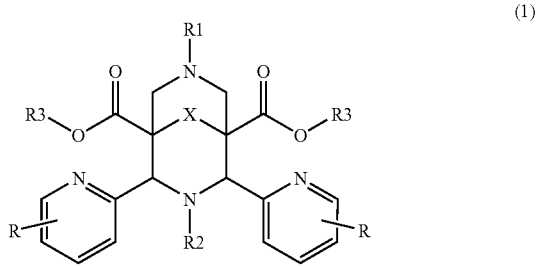

(1)

where R is hydrogen, hydroxyl, $C_1$-$C_4$ alkyl; R is $C_1$-$C_4$ alkyl, $C_6$-$C_{10}$ aryl or pyridinyl-$C_1$-$C_4$-alkyl; R is $C_1$-$C_4$ alkyl, $C_6$-$C_{10}$ aryl; R is $C_1$ $C_4$ alkyl and X is C=O or C(OH)$_2$.

Their use as a bleach catalyst in washing and cleaning compositions is claimed, inter alia, in WO 02/48301, US 2003/0 162 681 and WO 03/104234.

These compounds are prepared according to the information in Inorg. Chimica Acta, 337 (2002) 407-419, according to the following reaction scheme:

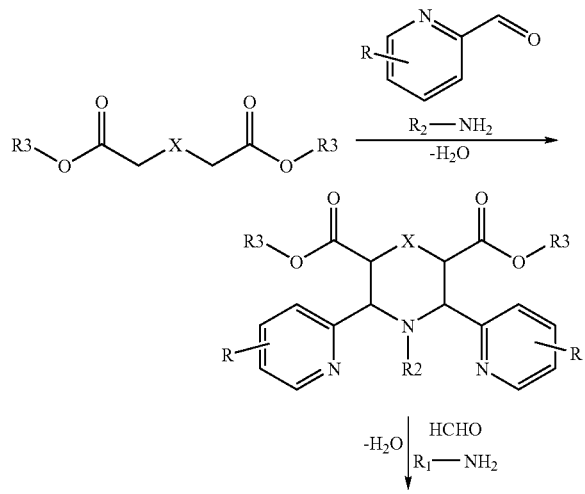

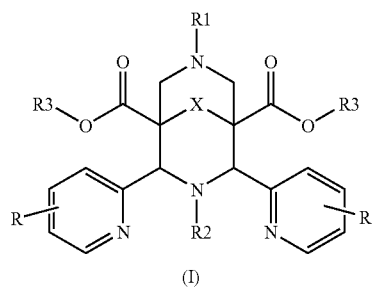

(I)

Starting from dicarboxylic diesters, compounds of the structural formula 1 are obtained in two Mannich condensation steps, in each case with elimination of water.

Performed on the laboratory scale, the synthesis is performed in methanol in the first reaction step; the isolation of the solid product by crystallization at temperatures around approx. 5° C. takes 1 to 3 days; the drying is effected at 40° C. under reduced pressure. In the second reaction step, the product of the first reaction step is suspended in ethanol, and amine and formaldehyde are added and heated to boiling. To isolate the product, the ethanol is drawn off, and the residue is taken up in ethanol, crystallized at approx. 5° C. and optionally recrystallized in ethanol.

The synthesis process described cannot be performed on the industrial scale; the solvent input is high, the crystallization takes too long, the isolation of the solid products from the reaction apparatus is problematic and cannot be performed industrially in this way, the yields have poor reproducibility.

It was therefore an object of the invention to develop an improved process for preparing substances of the formula I which is free of the disadvantages outlined above.

The invention provides a process for preparing 3,7-diazabicyclo[3.3.1]nonane compounds of the formula 1

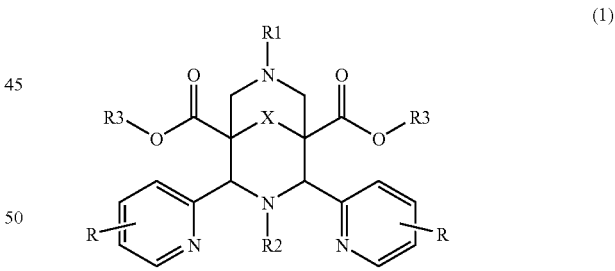

(1)

where R is hydrogen, hydroxyl, $C_1$-$C_4$ alkyl; R is $C_1$-$C_4$ alkyl, $C_6$-$C_{10}$ aryl; or pyridinyl-$C_1$-$C_4$-alkyl; R is $C_1$-$C_4$ alkyl, $C_6$-$C_{10}$ aryl; R is $C_1$ $C_4$ alkyl and X is C=O or C(OH)$_2$, by (a) reacting a dicarboxylic ester of the formula (2)

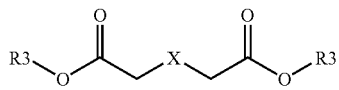

(2)

with a pyridinealdehyde of the formula (3)

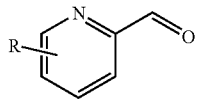

and an amine of the formula (4)

to give a piperidone of the formula (5)

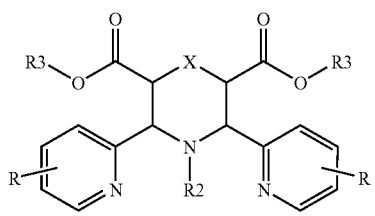

and (b) reacting the piperidones of the formula (5) thus obtained with formaldehyde and an amine of the formula $R^1$—$NH_2$, where R, $R^1$, $R^2$ and $R^3$ are each as defined above, which comprises performing reaction stage (a) in a $C_2$-$C_4$-alcohol and reaction stage (b) in a $C_3$-$C_4$-alcohol, and removing the water of reaction formed by azeotropic distillation.

Specifically, the process according to the invention is effected in the following manner:

Reaction Step (a)

The dicarboxylic diester is initially charged in a $C_2$-$C_4$-alcohol, for example ethanol, propanols or butanols, preferably in a branched $C_3$- or $C_4$-alcohol, and cooled to from 0° C. to 20° C. The pyridine-2-aldehyde in question is added dropwise to the cooled mixture. The amount of aldehyde is 2.0-2.2, preferably 2.0-2.1, molar equivalents based on the diester. The temperature in this step is generally 0-20° C., preferably 5-15° C., more preferably 5-10° C. The metered addition is effected within 5-45 minutes, preferably within 10-20 minutes. Subsequently, the primary amine $R_2$—$NH_2$ is added dropwise. The amount of amine is 0.9-1.1, preferably 0.95-1.05, molar equivalents based on the diester. The temperature in the course of this metered addition is generally 0-20° C., preferably 5-15° C., more preferably 5-10° C. The addition is effected over a period of 30-120 minutes, preferably within 60-90 minutes. After the addition has ended, the reaction mixture is heated and the content of water in the mixture is reduced by azeotropic distillation under reduced pressure. The internal temperature during the distillation is 40-60° C., preferably 45-50° C. The vacuum is adjusted correspondingly. Subsequently, the mixture is cooled and stirred further, in the course of which the temperature is 0-20° C. After the continued stirring time has ended, the product is filtered off, washed with solvent and dried.

In the process according to the invention, the intermediate is obtained in yields of >80%, preferably in yields of 84-88%, and high purity (content>95% by NMR).

Reaction Step (b)

The product of the first stage is in turn suspended in a $C_3$-$C_4$-alcohol, for example in propanols or butanols, preferably branched $C_3$- or $C_4$-alcohols. The alcohol in this reaction step is preferably the same alcohol as in reaction step (a). However, it is also possible to take different alcohols within the given definition in the two reaction steps. The amine $R^1$—$NH_2$ and formalin solution are added successively. The amount of amine is 1.2-1.6, preferably 1.4-1.5, molar equivalents based on the intermediate; the amount of formaldehyde is 3.0-4.5 molar equivalents based on the product of the first stage. Subsequently, the mixture is heated and stirred further. The reaction time is 1-3 hours, preferably 1.5-2 hours; the temperature is 50-70° C., preferably 55-65° C. Subsequently, the content of water in the reaction mixture is reduced as far as possible by azeotropic distillation under reduced pressure. After the distillation has ended, the mixture is first cooled to room temperature, then to 0-15° C., preferably to 5-10° C., and stirred further. The product is then filtered off, washed with fresh solvent and dried.

In the process according to the invention, the compound of the formula I is obtained in yields of >50%, preferably in yields of 55-65%, in high purity (content>98% by NMR).

Compared to the prior art, the preparation of the compounds of the formula 1 by the process according to the invention requires only one organic solvent instead of two and
a mass of organic solvent required reduced to approximately 35%.

Compared to the prior art, the process can be performed on the industrial scale.

The process as described in the literature cannot be implemented on the industrial scale for many reasons; the crystallization took a long time and is barely reproducible. Introduction of the distillation in stage 1 and 2 succeeded in defining clearly defined parameters for a reproducible crystallization within a reduced time; the time saving is approximately 80%. The examples which follow are intended to illustrate the present invention in detail without restricting it thereto.

EXAMPLE 1

1st stage: 12.9 kg of dimethyl acetonedicarboxylate (97%; 72 mol) were dissolved in 52.5 l of isobutanol. The solution was cooled to 10° C. At this temperature, 15.4 kg of pyridine-2-aldehyde (14.4 mol) were added dropwise and the mixture was stirred for a further 10 minutes. Subsequently, 5.59 kg of methylamine (40% in water, 72 mol) were added dropwise to this mixture at such a rate that the temperature could be maintained with uniform cooling. The reaction mixture was stirred at 10° C. for a further 90 minutes. After the reaction time had ended, the mixture was heated to 40-45° C. and 6.6 kg of water phase were separated out under reduced pressure at internal temperature 40-45° C. with the aid of a water separator. The mixture was then vented and cooled to 5-10° C. The product was filtered off and washed with 7.5 l of isobutanol. The moist product was dried at 50° C. under reduced pressure. 24.3 kg (88%) of 1-methyl-2,6-dipyridyl-3,5-di(methoxy-carbonyl)-4-piperidone were obtained as a white-beige powder.

2nd stage: 23 kg of the product of the 1st stage (60 mol) were initially charged in 40 l of isobutanol. First 9.73 kg of aminomethylpyridine (90 mol) then 19.32 kg of formaldehyde solution (37%, 24 mol) were added to this suspension at room temperature. After the addition had ended, the mixture was heated to 55-60° C. and stirred at this temperature for 2 hours. Subsequently, at a maximum internal temperature of 60° C., first 16 kg of water phase were separated out with the aid of a water separator, and then additionally 4 kg of isobutanol phase were distilled off. After the distillation had ended, the mixture was vented and cooled first to room temperature, then to 5-10° C. After stirring at 5-10° C. for 2 h, the precipitate was filtered off, washed with 7.5 l of isobutanol and dried at 50° C. under reduced pressure. 19.8 kg (64%) of 2,4-di (pyridyl)-3-methyl-7-(pyridin-2-ylmethyl)-3,7-diazabicyclo[3.3.1]nonan-9-one 1,5-dimethyldicarboxylate were obtained in the form of an off-white powder.

Yield over 2 stages: 56.3%.

EXAMPLE 2

1st stage: 44.89 g of dimethyl acetonedicarboxylate (97%; 0.25 mol) were initially charged in 125 ml of isobutanol. The mixture was cooled to 9° C. At this temperature, first 53.55 g of pyridine-2-aldehyde (0.5 mol) were added dropwise. Subsequently, 27.03 g of aminomethylpyridine (0.25 mol) were added dropwise at such a rate that the temperature could be maintained. The mixture was then heated to approximately 50° C., and approx. 65 ml of isobutanol-water mixture were distilled off under reduced pressure at internal temperature approx. 50° C., in the course of which approx. 65 ml of fresh isobutanol were simultaneously metered in. After the distillation had ended, the mixture was vented and cooled to 20° C. The product was filtered off, washed repeatedly with isobutanol and dried at 50° C. under reduced pressure. 100.6 g (87.4%) of 1-(pyridin-2-ylmethyl)-2,6-dipyridyl-3,5-di(methoxycarbonyl)-4-piperidone were obtained as a beige-white powder.

2nd stage: 69 g of the product of the 1st stage (0.15 mol) were initially charged in 100 ml of isobutanol. At room temperature, first 18.0 g of methylamine (40% aqueous solution, 0.225 mol), then 48.7 g of formaldehyde solution (37% in water, 0.6 mol) were added. The mixture was heated to 60° C. and stirred at this temperature for 2 h. After the reaction time had ended, approx. 200 ml of isobutanol-water mixture were distilled off under reduced pressure at internal temperature 60° C., in the course of which 150 ml of fresh isobutanol were simultaneously added dropwise. After the distillation had ended, the mixture was vented, and cooled first to room temperature, then to 5° C. The mixture was stirred at 5° C. for several more hours. Subsequently, the product was filtered off, washed with isobutanol and dried at 50° C. under reduced pressure. 38.7 g (51%) of 2,4-di(pyridyl)-3-(pyridin-2-ylmethyl)-7-methyl-3,7-diaza-bicyclo[3.3.1]nonan-9-one 1,5-dimethyldicarboxylate were obtained as a beige-white powder.

Yield over 2 stages: 44.6%.

The invention claimed is:

1. A process for preparing 3,7-diazabicyclo[3.3.1]nonane compounds of the formula 1

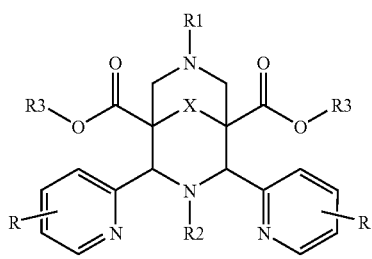

(1)

where R is hydrogen, hydroxyl, $C_1$-$C_4$ alkyl; $R^1$ is $C_1$-$C_4$ alkyl, $C_6$-$C_{10}$ aryl, pyridinyl-$C_1$-$C_4$-alkyl; $R^2$ is $C_1$-$C_4$ alkyl, $C_6$-$C_{10}$ aryl; $R^3$ is $C_1$-$C_4$ alkyl and X is C=O or $C(OH)_2$, by (a) reacting a dicarboxylic ester of the formula (2)

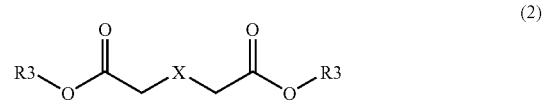

(2)

with a pyridinealdehyde of the formula (3)

(3)

and an amine of the formula (4)

(4)

to give a piperidone of the formula (5)

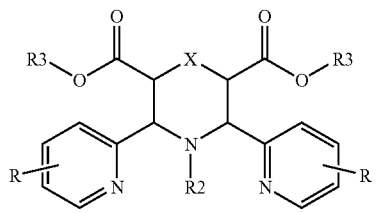

(5)

and (b) reacting the piperidones of the formula (5) thus obtained with formaldehyde and an amine of the formula $R^1$—$NH_2$, where R, $R^1$, $R^2$ and $R^3$ are each as defined above, which comprises performing reaction stage (a) in a $C_2$-$C_4$-alcohol and reaction stage (b) in a $C_3$-$C_4$-alcohol, and removing the water of reaction formed by azeotropic distillation.

2. The process as claimed in claim 1, wherein reaction stages (a) and (b) are performed in a branched $C_3$- or $C_4$-alcohol.

3. The process as claimed in claim 1, wherein reaction stages (a) and (b) are performed in butanol.

* * * * *